US008329965B2

(12) United States Patent
Matthews et al.

(10) Patent No.: US 8,329,965 B2
(45) Date of Patent: Dec. 11, 2012

(54) METHOD AND SYSTEM FOR PREVENTING CLATHRATE HYDRATE BLOCKAGE FORMATION IN FLOW LINES BY ENHANCING WATER CUT

(75) Inventors: Patrick N. Matthews, Cypress, TX (US); Sivakumar Subramanian, Houston, TX (US); Jefferson L. Creek, Katy, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 12/943,455

(22) Filed: Nov. 10, 2010

(65) Prior Publication Data

US 2011/0136700 A1    Jun. 9, 2011

Related U.S. Application Data

(63) Continuation of application No. 10/740,265, filed on Dec. 17, 2003, now abandoned.

(51) Int. Cl.
*C09K 8/52* (2006.01)

(52) U.S. Cl. ............................................. 585/15; 507/90

(58) Field of Classification Search ...................... 585/15
See application file for complete search history.

(56) References Cited

U.S. PATENT DOCUMENTS

| | | |
|---|---|---|
| 3,975,167 A | 8/1976 | Nierman |
| 5,491,269 A | 2/1996 | Colle et al. ...................... 585/15 |
| 5,536,893 A | 7/1996 | Gudmundsson |
| 5,941,096 A | 8/1999 | Gudmundsson |
| 5,998,681 A | 12/1999 | Rojey |
| 6,080,704 A | 6/2000 | Halliday et al. .............. 507/136 |
| 6,082,118 A | 7/2000 | Endrizzi et al. |
| 6,111,155 A | 8/2000 | Williams et al. |
| 6,180,843 B1 | 1/2001 | Heinemann et al. |

(Continued)

OTHER PUBLICATIONS

Sinquin, A. Bredzinsky, X., Beunat, V., "Kinetic of Hydrates Formation: Influence of Crude Oils", *Society of Petroleum Engineers* (SPE 71543), pp. 1-12, 2001.

(Continued)

*Primary Examiner* — Ellen McAvoy
(74) *Attorney, Agent, or Firm* — Merchant & Gould (57) ABSTRACT

The present invention includes a method for inhibiting hydrate formation blockage in a flow line used to transport hydrocarbon containing fluids. Water is added to a hydrocarbon containing fluid to produce a water cut enhanced hydrocarbon containing fluid. Salt may be added to the hydrocarbon containing fluids as well. Hydrate formation blockage is inhibited from forming within the flow line by the addition of the water and/or the salt. Sufficient water may be added such that the hydrocarbon containing fluid is converted from a water in oil emulsion to a water continuous emulsion. A system for preventing the formation of hydrate blockage in conduits is also provided. The system includes a flow line for transporting a hydrocarbon containing fluid and a water injection conduit fluidly connected to the flow line to add water to the flow line to increase the water cut of a hydrocarbon containing fluid flowing through the flow line. A salt dispenser may also be included which is used to increase the salinity of the hydrocarbon containing fluid. The system may further include a water separator to separate hydrocarbons from water which receives fluids from the flow line. The flow line, water separator and water injection conduit may cooperate to form a loop wherein water from the flow line may be separated by the water separator and a portion of the separated water is delivered back to the water injection conduit to be reinjected into the flow line.

26 Claims, 7 Drawing Sheets

U.S. PATENT DOCUMENTS

| | | |
|---|---|---|
| 6,194,622 B1 | 2/2001 | Peiffer et al. ............... 585/15 |
| 6,222,083 B1 | 4/2001 | Colle ............................ 585/15 |
| 6,281,274 B1 | 8/2001 | Bakeev et al. ............... 524/376 |
| 6,350,928 B1 | 2/2002 | Waycullis et al. |
| 6,417,417 B1 | 7/2002 | Sinquin et al. |
| 6,451,892 B1 | 9/2002 | Bakeev et al. ............... 524/386 |
| 6,464,009 B2 | 10/2002 | Bland et al. ................. 166/300 |
| 6,774,276 B1 | 8/2004 | Lund et al. .................. 585/899 |
| 6,939,832 B2 | 9/2005 | Collins ........................ 507/225 |
| 2002/0031156 A1 | 3/2002 | Kidokoro et al. |
| 2002/0120172 A1 | 8/2002 | Waycullis et al. |
| 2006/0272805 A1* | 12/2006 | O'Malley et al. .......... 166/177.2 |
| 2009/0221451 A1* | 9/2009 | Talley ............................ 507/90 |
| 2010/0051279 A1* | 3/2010 | Baugh et al. ................. 166/302 |
| 2010/0252260 A1* | 10/2010 | Fowler et al. ................ 166/275 |

OTHER PUBLICATIONS

Larsen, R., Lund, A., Andersson, VL., Hjarbo, K.W., "Conversion of Water to Hydrate Particles", *Society of Petroleum Engineers* (SPE 71550), pp. 1-5, 2001.

* cited by examiner

METHOD AND SYSTEM FOR PREVENTING CLATHRATE HYDRATE BLOCKAGE FORMATION IN FLOW LINES BY ENHANCING WATER CUT

CROSS-REFERENCE TO RELATED APPLICATION

This application is a continuation of U.S. patent application Ser. No. 10/740,265, filed Dec. 17, 2003, the contents of which are incorporated herein by reference in its entirety.

TECHNICAL FIELD

The present invention relates to preventing the formation of clathrate hydrate blockages in flow lines or conduits carrying hydrocarbons.

BACKGROUND OF THE INVENTION

Clathrate hydrate plug formation in oil and gas pipelines is a severe problem for the petroleum industry. When water is produced along with gas, oil, or mixtures of both, under the right pressure and temperature conditions, there is a potential to form a solid hydrate phase. Pressure-temperature conditions favorable for hydrate formation are commonly encountered during the winter in fields onshore and in shallow water depths offshore, and regularly in deepwater (>1,500 feet water depth) fields offshore. As a rule of thumb, at a seafloor temperature of about 40° F. for water depths greater than 3,000 feet, hydrates can form in a typical natural gas pipeline at pressures as low as 250 psi. As solid hydrates form, the hydrates can deposit on the pipe walls or agglomerate into larger solid masses creating obstructions to flow.

Technologies currently used to prevent hydrate blockage formation include dehydration, heat and/or pressure management or chemical injection with thermodynamic or low dosage hydrate inhibitors (LDHI). Dehydration is simply removing most of the water from the hydrocarbon stream so that too little is left to form hydrate blockages. Temperature or pressure control is used to operate a system outside of conditions that can promote hydrate formation. The addition of thermodynamic inhibitors (typically alcohols, glycols or salts) produces an anti-freeze like effect that shifts the hydrate phase equilibrium condition to lower temperatures at a given pressure so that a system may be operated safely outside the hydrate stability region. LDHI act in one of two ways: 1) as a kinetic inhibitor, or 2) as an anti-agglomerant. Kinetic LDHIs merely slow the hydrate formation rate so that formation of a solid blockage is retarded during the residence time of the fluids in the pipeline. Anti-agglomerant LDHIs allow the hydrates to form, but keep the hydrate particles dispersed in a liquid hydrocarbon phase. Anti-agglomerant LDHIs are also known to have limitations on the water cut in which the chemicals can work. They are usually recommended for application for water cuts of less than 50%.

Each of these solutions for hydrate prevention can work, but all require significant capital or operating expense. The thermal and dehydration options are capital intensive, the thermodynamic inhibitor options are both capital and operationally intensive, and the LDHI option is operationally intensive. LDHIs also have additional risk associated with their application due to the relative immaturity of the technology. Additionally, discharge water quality (toxicity) and crude quality (methanol content for example) issues can be a concern when using both thermodynamic inhibitors and LDHIs. There is also a general concern in the industry that as remote deepwater fields mature, water cuts may become high to the point where chemical injection for hydrate inhibition may offer considerable challenges—either due to the sheer volumes of thermodynamic inhibitor required or due to limitations on LDHI performance as mentioned above. Therefore, the issue of a cost-effective and reliable hydrate inhibition strategy for fields with high water cuts is a major challenge facing the industry.

There are additional flow assurance issues commonly found with low-temperature high pressure flow in flow lines. In cases where there is water in an oil emulsion, such an emulsion can have high viscosity leading to problems associated with excessive pressure drop. The present invention, to be described hereafter, addresses the challenges described above.

SUMMARY OF THE INVENTION

The present invention includes a method for inhibiting hydrate formation blockage in flow lines used to transport hydrocarbon containing fluids. Water is added to a hydrocarbon containing fluid to produce a water cut enhanced hydrocarbon containing fluid. The water cut enhanced hydrocarbon containing fluid is then transported by a flow line. Hydrate formation blockage is inhibited from forming within the flow line by the addition of the water which tends to lower the hydrate phase equilibrium temperature for a given pressure of the hydrocarbon containing fluid and flow velocity.

Preferably, the resulting water cut enhanced hydrocarbon containing fluid is water continuous. Sufficient water may be added such that the hydrocarbon containing fluid is inverted from a water in oil emulsion to a water continuous emulsion state thereby decreasing emulsion viscosity and reducing pressure drop in the flow line.

Sufficient water may be added such that the water cut of the water cut enhanced hydrocarbon containing fluid is at least 50%, and possibly even 75% or 85%. The hydrate thermal equilibrium temperature of the water cut enhanced hydrocarbon containing fluid may be lowered 2.5° F., 5.0° F., or even 10° F. as compared to the original hydrocarbon containing fluid.

Further, sufficient water may be added to the original hydrocarbon containing fluid such that there is an excess of the water phase relative to the hydrocarbon phase such that hydrate formation is self limiting. This occurs when the hydrocarbon hydrate forming components are exhausted through hydrate formation and a flowing slurry of hydrates, hydrocarbons and water results.

Salt may be added to increase the salinity of the water cut enhanced hydrocarbon containing fluid. The weight % of salt in the water cut enhanced hydrocarbon containing fluid may be 5%, 10% or even 15% or higher.

A system for preventing the formation of hydrate blockage in flow lines is also provided. The system includes a flow line for transporting a hydrocarbon containing fluid and a water injection conduit fluidly connected to the flow line to add water to the flow line to increase the water cut of the fluid flowing through the flow line. The flow line should be connected to a hydrocarbon source and the water injection conduit fluidly connected to a water source. The system may be operable in an environment sufficiently cool such that hydrate blockage might form absent the addition of water to the hydrocarbon containing fluid from the water injection conduit. The hydrocarbon source may be a well bore from which hydrocarbons are produced. The water source may sea water, a sub sea water well or a water storage tank mounted on an offshore platform. Alternatively, the system may be used on land where hydrocarbon containing fluids are to be transported in flow lines and the flow lines are exposed to cold temperatures.

The system may further include a water separator to separate water from hydrocarbons received from the flow line. The flow line, water separator and water injection conduit may cooperate to form a partially closed loop wherein water from the flow line may be separated by the water separator and delivered back to the water injection conduit to be reinjected into the flow line to enhance the water cut of the hydrocarbon containing fluid.

It is an object of the present invention to provide a method and system to address multiple flow assurance issues (hydrate inhibition, emulsion viscosity/stability, system thermal performance, and system hydraulic performance) through a simple, cost-effective, and environmentally friendly strategy.

It is another object to provide a method for multiphase production of crude oil and natural gas wherein hydrocarbon containing fluids are transported through a flow line at unconventionally high water cuts to thereby reduce hydrate blockages in the flow line relative to using hydrocarbon containing fluids having a lower water cut.

BRIEF DESCRIPTION OF THE FIGURES OF THE DRAWINGS

These and other objects, features and advantages of the present invention will become better understood with regard to the following description, pending claims and accompanying drawings where:

DETAILED DESCRIPTION OF THE EMBODIMENTS

The present invention is counterintuitive and surprising in that it calls for adding excess water to a hydrocarbon containing fluid to inhibit hydrate blockage formations in flow lines of a system. Conventional wisdom is to remove water and/or add chemical hydrate inhibitors. This process of purposely adding water, which is abundantly available in offshore operations, may be a cost-effective, reliable hydrate blockage inhibition strategy with several potential additional side benefits. The present invention may also be used on land as well to inhibit hydrate formation blockages where hydrocarbon containing fluids are transported along a flow line exposed to cold temperatures.

This invention applies to multiphase flow systems where formation of hydrate plugs or other significant hydrate obstructions in flow lines are a concern. Ideally, water, and possibly salt or brine, is added to a hydrocarbon containing fluid such that a water continuous phase is present (high water cut). The addition of the water and salt to the hydrocarbon containing fluid ideally addresses multiple flow assurance issues (hydrate inhibition, emulsion viscosity/stability, system thermal performance, and system hydraulic performance) through a simple, cost-effective, and environmentally friendly strategy.

Following this strategy, injection of water could be used to operate systems in a water continuous emulsion state, thereby decreasing emulsion viscosity and reducing pressure drops in pipe lines or flow lines. This could be beneficial especially for heavy oils that may be prone to forming high viscosity water in oil emulsions at cold sub sea conditions. Further, if a high salinity brine is injected instead of fresh water, separation problems topside due to emulsions could be potentially alleviated, or at least reduced, since salt can have an emulsion breaking effect depending on the characteristics of the emulsion.

Recent evidence discovered through experiments and modeling with heavy oils (.about.20.degree. API) suggests that hydrate equilibrium temperatures are reduced as water cut increases. The term "hydrate equilibrium temperature" means the temperature at which hydrates will readily form for a given composition of a hydrocarbon containing fluid at a particular pressure and flow rate. The effect of increasing water cut to lower hydrate equilibrium temperature can be found in most hydrocarbon systems and is unique for each particular composition of hydrocarbon containing fluid. For example, compositions may contain mostly natural gas or else predominantly heavy oils. The effect is more pronounced for heavy oils which tend to have low GORs (gas-to-oil ratio) and low bubble points.

Figure 1:
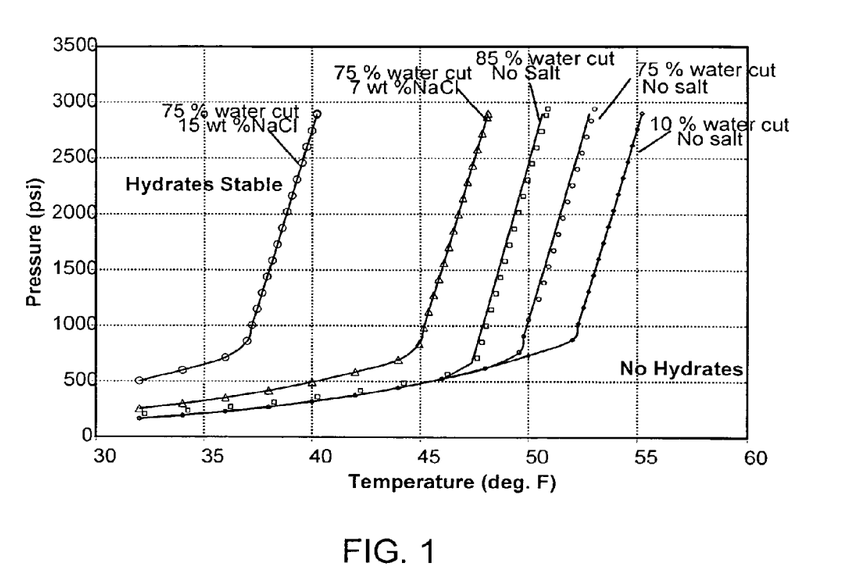
FIG. 1 is a graph showing the thermodynamic effect of water cut and brine salinity on the hydrate stability region of a heavy oil.

FIG. 1 shows the thermodynamic effect of water cut and brine salinity on the hydrate stability region of a heavy oil (.about.20.degree. API). In this example, increasing the water cut (no salt present) from 10% to 75% reduces hydrate equilibrium temperature at pressures above the bubble point by approximately 2.5° F.; increasing the water cut from 75% to 85% reduces the hydrate equilibrium temperature by another 2.2° F.

Also, illustrated is the enhanced thermodynamic effect achieved by adding brine instead of fresh water to lower the thermal equilibrium temperature. For the heavy oil, increasing the water cut from 10% to 75% by adding brine with 7 weight % NaCl, as opposed to water with no salt, reduces hydrate equilibrium temperature above the bubble point by 7° F. compared to 2.5° F. when adding fresh water only. Adding brine with 15 weight % NaCl reduces the hydrate equilibrium temperature above the bubble point by 15° F. compared to the 10% water cut, fresh water case.

Figure 2:
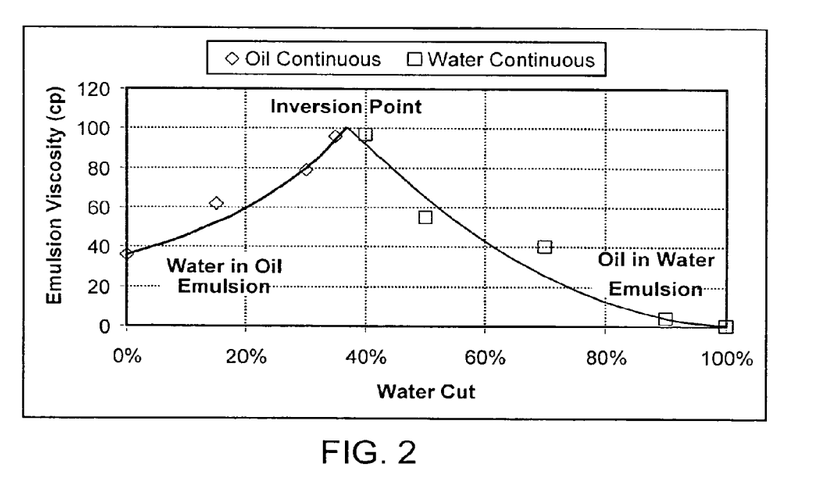
FIG. 2 is a graph showing the general change in viscosity of emulsions as a function of water cut.

FIG. 2 shows a general change in viscosity of emulsions as a function of water cut. As water cut is increased, a water in oil emulsion can be converted to an oil in water emulsion. The graph shows that viscosity of a water in oil emulsion is usually considerably higher than that of an oil in water emulsion at high water cuts (> than 70% water cut). This is especially pronounced in case of heavy oil systems. At water cuts as high as 90%, viscosity is close to that of water.

In addition to the above thermodynamic effect, it is anticipated that by having an excess of the water phase relative to the hydrocarbon phase in these high water fraction systems, any hydrate formation reaction would be self limiting as hydrate forming components (lighter hydrocarbons) in the flow stream are exhausted. The result is expected to be an oil and hydrate in water slurry. Within certain operating conditions of fluid flow velocity, system geometry, water cut, and temperature and pressure the oil and hydrate in water slurry should remain flowable.

As already mentioned, brine also enhances the thermodynamic effect on hydrate stability produced by adding water to the system. Water also improves heat retention thereby improving thermal performance of the system which might be helpful for mitigating certain flow assurance issues. Switching to water or high salinity brine injection as the hydrate inhibition strategy is also expected to reduce chemical inhibitor presence in water and the oil phase. This will have significant benefits for topside water clean up and should result in reduced penalties imposed on an operator by downstream refineries due to the elimination of methanol from crude oil. Therefore, the proposed strategy is also a more environmentally friendly hydrate inhibition strategy as compared to the current thermodynamic and/or LDHI inhibitor injection strategy since storage, handling, and processing of flammable (methanol), potentially toxic (anti-agglomerant LDHIs) chemicals can be eliminated from offshore operations.

Figure 3:
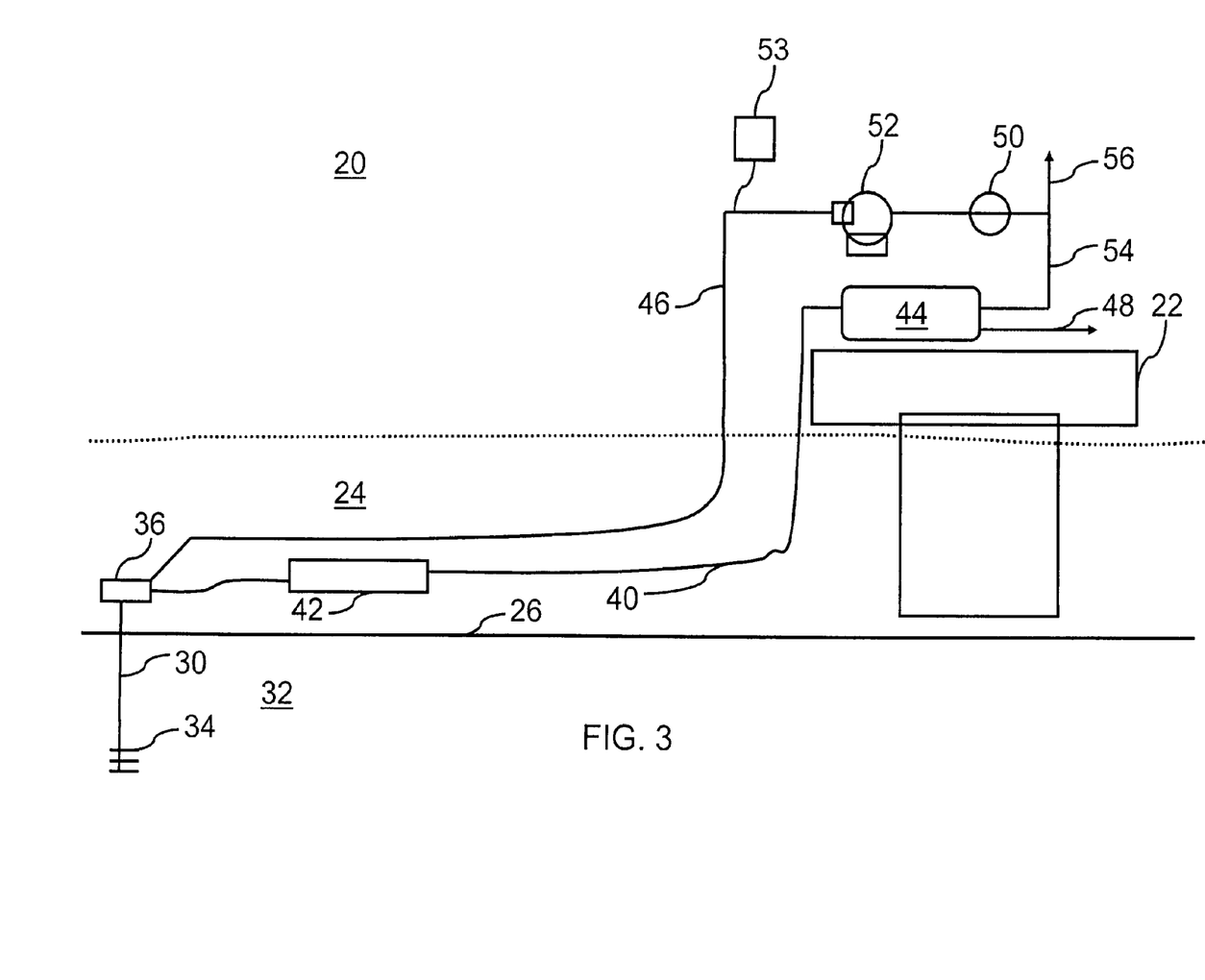
FIG. 3 is a first embodiment of a hydrate blockage inhibiting system which includes a water injection conduit which injects water and/or salt into a sub sea wellhead tree to enhance the water cut of a hydrocarbon containing fluid carried by a flow line to a floating platform in a sea.

FIG. 3 illustrates a first exemplary embodiment of a hydrate blockage inhibition system 20 which is constructed in accordance with the present invention. An offshore platform 22 is located in a sea 24 disposed above a sea floor 26. A well bore 30 is located in a sub sea formation 32. Perforations 34 in well bore 30 allow hydrocarbon containing fluids to be extracted from formation 32. Located atop well bore 30 is a sub sea tree 36. Tree 36 passes a hydrocarbon containing fluid from well bore 30 to a production flow line or pipeline 40. A sub sea manifold 42 is disposed intermediate tree 36 and platform 22.

Platform 22 supports a separator 44 which separates water from the hydrocarbon containing fluid received from flow line 40. The separated water may be disposed of in conventional fashions such as dumping the water into sea 24 after being cleaned to an environmentally acceptable quality. Alternatively, a substantial portion of the separated water or brine solution may be directed to a water injection flow line 46 which supplies water to be added to the hydrocarbon containing fluid received from well bore 30. In this instance, the added water is injected into a port (not shown) plumbed into tree 36. Separated oil exits from separator 44 through an oil discharge line 48. Although, not shown, a separate gas discharge line may also be employed when substantial amounts of gas are produced and are separated by separator 44.

A meter 50 measures and controls the quantity of water which is being passed from separator 44 to a pump 52. Pump 52 is used to increase pressure in the water passing through water injection conduit 46 and which is injected into the produced hydrocarbons from well bore 30. Salt may also be added to water injection flow line 46 from a salt dispenser 53, preferably as a brine such as a sodium chloride in water solution. In this exemplary embodiment, the water is injected into tree 36. A water conduit 54 connects separator 44 and pump 52. A water discharge conduit 56 is used to discharge surplus separated water which is not to be reinjected to enhance the water cut of the produced hydrocarbon containing fluid from well bore 30.

The produced hydrocarbon containing fluid from well bore 30 typically arrives at tree 36 from well bore 30 at a particular pressure and at a temperature which is significantly above the temperature suitable for hydrate formation. However, as the produced fluid travels to sub sea manifold 42 and up production flow line 40, the cold sea waters surrounding flow line 40 may cool the produced hydrocarbon containing fluid sufficiently that hydrate formation blockage may be a significant possibility. That is, the production hydrocarbon containing fluids may enter into the hydrate stability region for the particular composition of oil, gas, water, and other constituents of the produced fluids from well bore 30.

In operation, the amount of water/brine solution added to the produced hydrocarbon containing fluid is dependent on the desired characteristics of the water cut enhanced hydrocarbon containing fluid. For example, if the produced hydrocarbon containing fluid from well bore 30 is at a low water cut, i.e., the produced fluid is an oil emulsion containing water or has a hydrocarbon continuous phase, then sufficient water/brine solution may be added to invert the fluid into a water continuous, water cut enhanced hydrocarbon containing fluid. This addition of water may be sufficient to drop the hydrate equilibrium temperature 2.5° F., 5.0° F., 10° F. or even 15° F., depending on how much water and salt is added to the production fluids being injected into tree 36. Also, it may be permissible to allow hydrate formation to readily occur if sufficient water and salt are added to maintain the water cut enhanced production fluid in a slurry state where individual hydrate particles are suspended in a water continuous fluid. Accordingly, blockages formed by hydrates will be avoided in production pipeline 40 which might otherwise occur absent the addition of the water and/or brine to the produced fluids from well bore 30.

Figure 4:
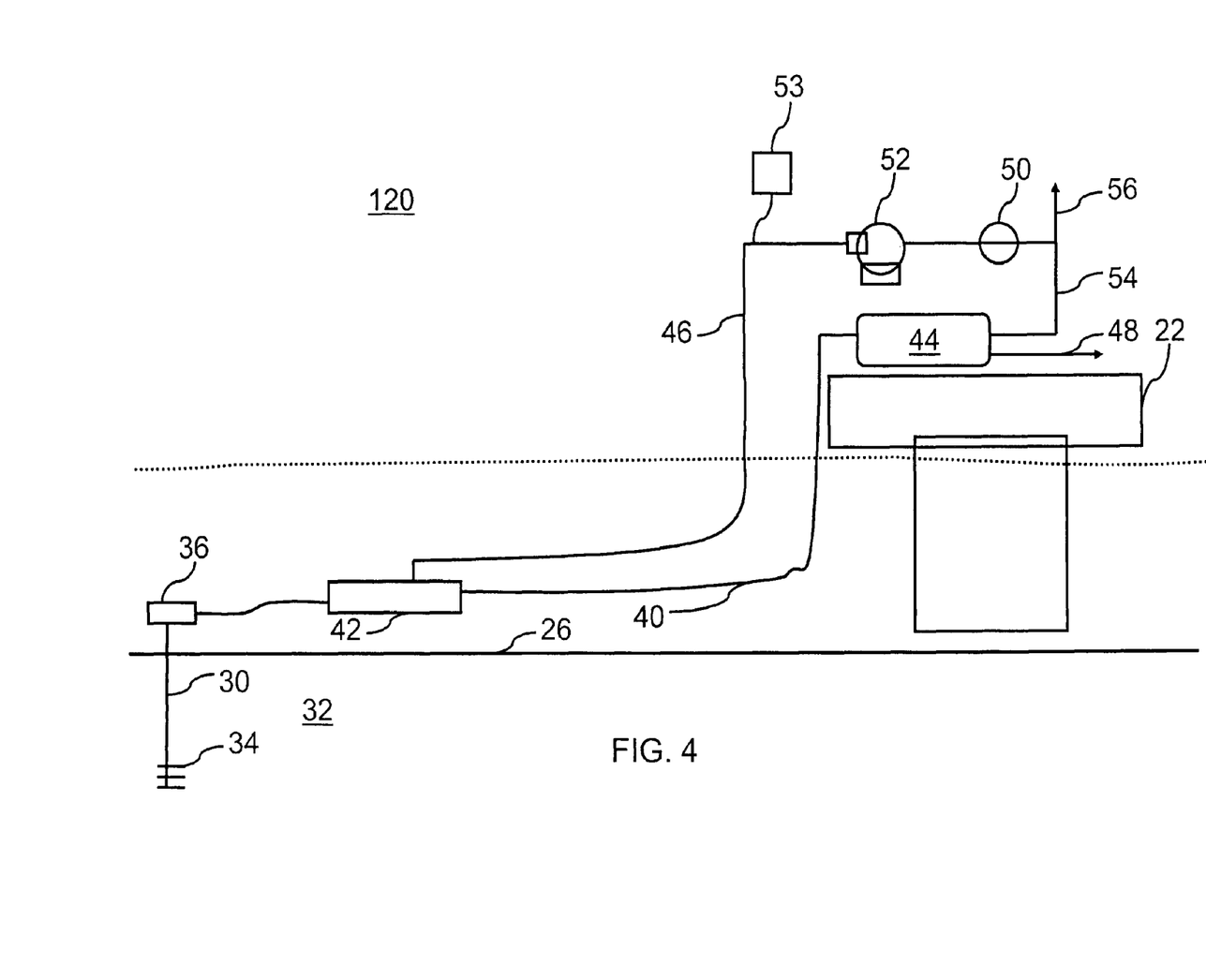
FIG. 4 is a second embodiment of a hydrate blockage inhibiting system which includes water injection into a sub sea manifold.

FIG. 4 shows a second exemplary embodiment of a system 120 which is similar to that of the first embodiment shown in FIG. 1. Like components of the system have been given the same reference numerals as in the first embodiment. In this instance, the added water/salt is added downstream of the tree 36 with injection occurring into sub sea manifold 42.

Figure 5:
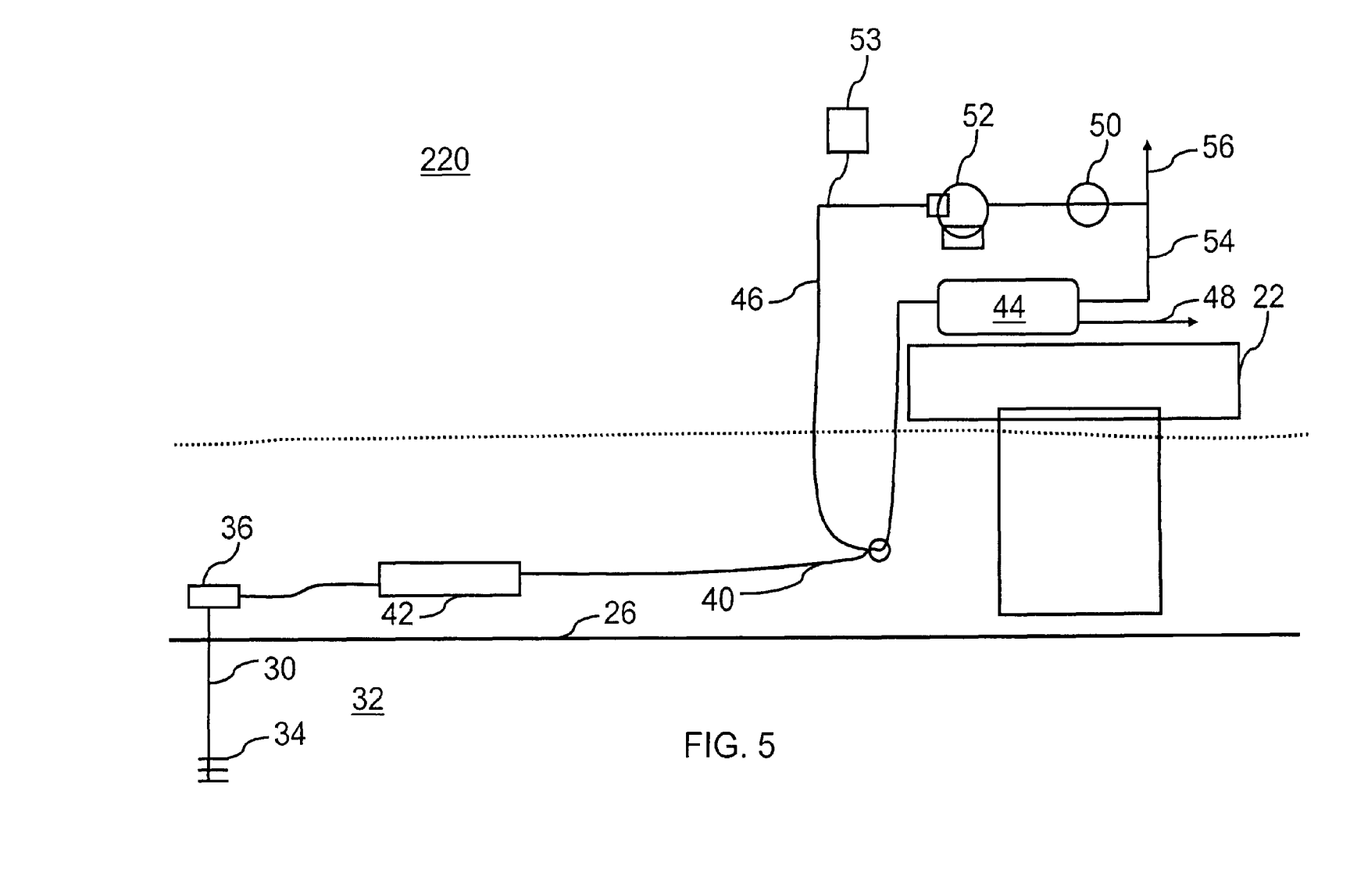
FIG. 5 is a third embodiment of a hydrate blockage inhibiting system which includes water injection at a riser base.

FIG. 5 shows a third embodiment of a system 220 wherein water/salt is injected downstream of tree 36 and sub sea manifold 42 directly into the production pipeline at the base of a riser. The added water/salt should be injected into production pipeline sufficiently upstream of where the cold sea water could potentially drop the temperature of the production fluid to where hydrate phase stability conditions may exist. Accordingly, the beneficial effects provided by the introduction of added water and salt should be obtained before hydrate formation blockage can occur.

Figure 6:
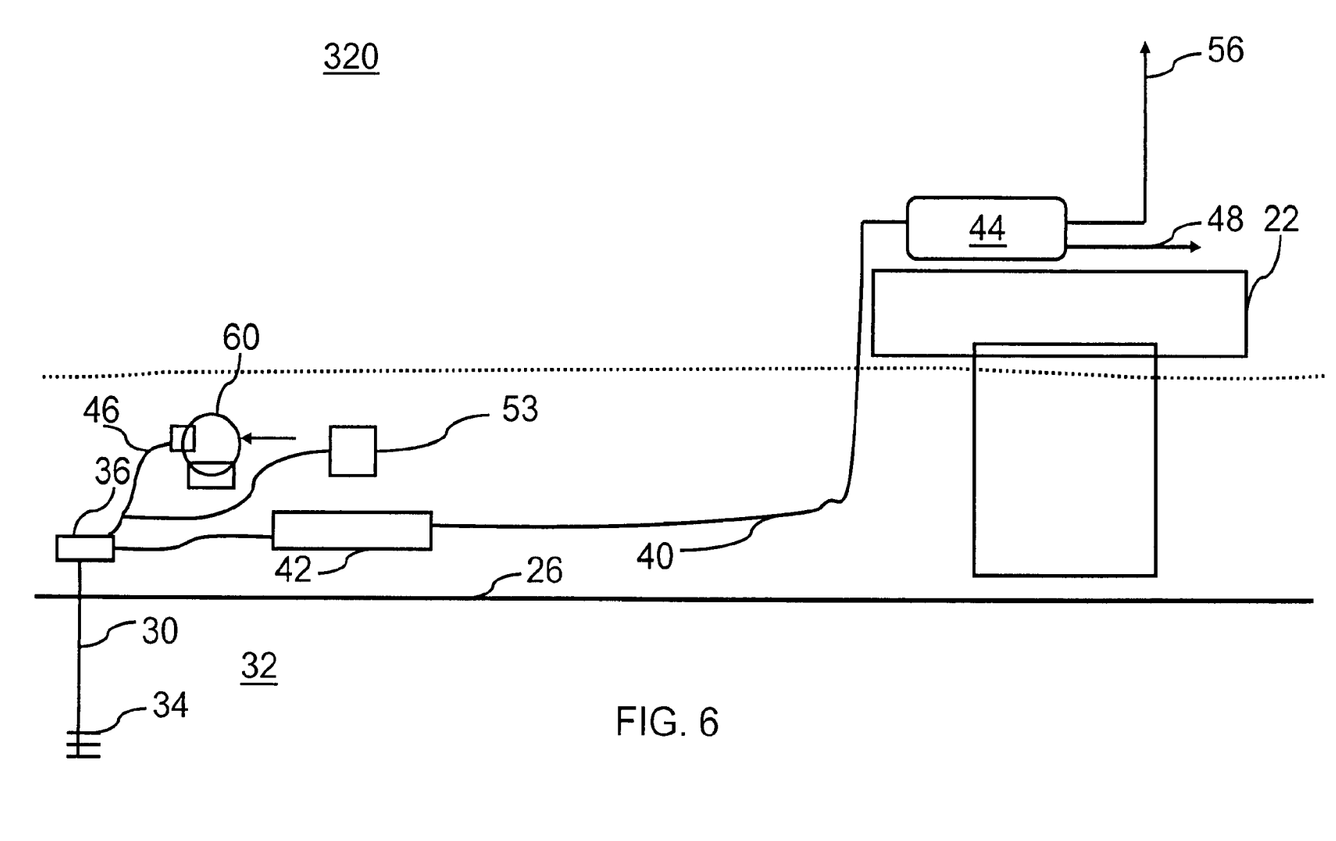
FIG. 6 is a fourth embodiment of a hydrate blockage inhibiting system using a submersible pump to inject sea water into a wellhead tree.
Figure 7:
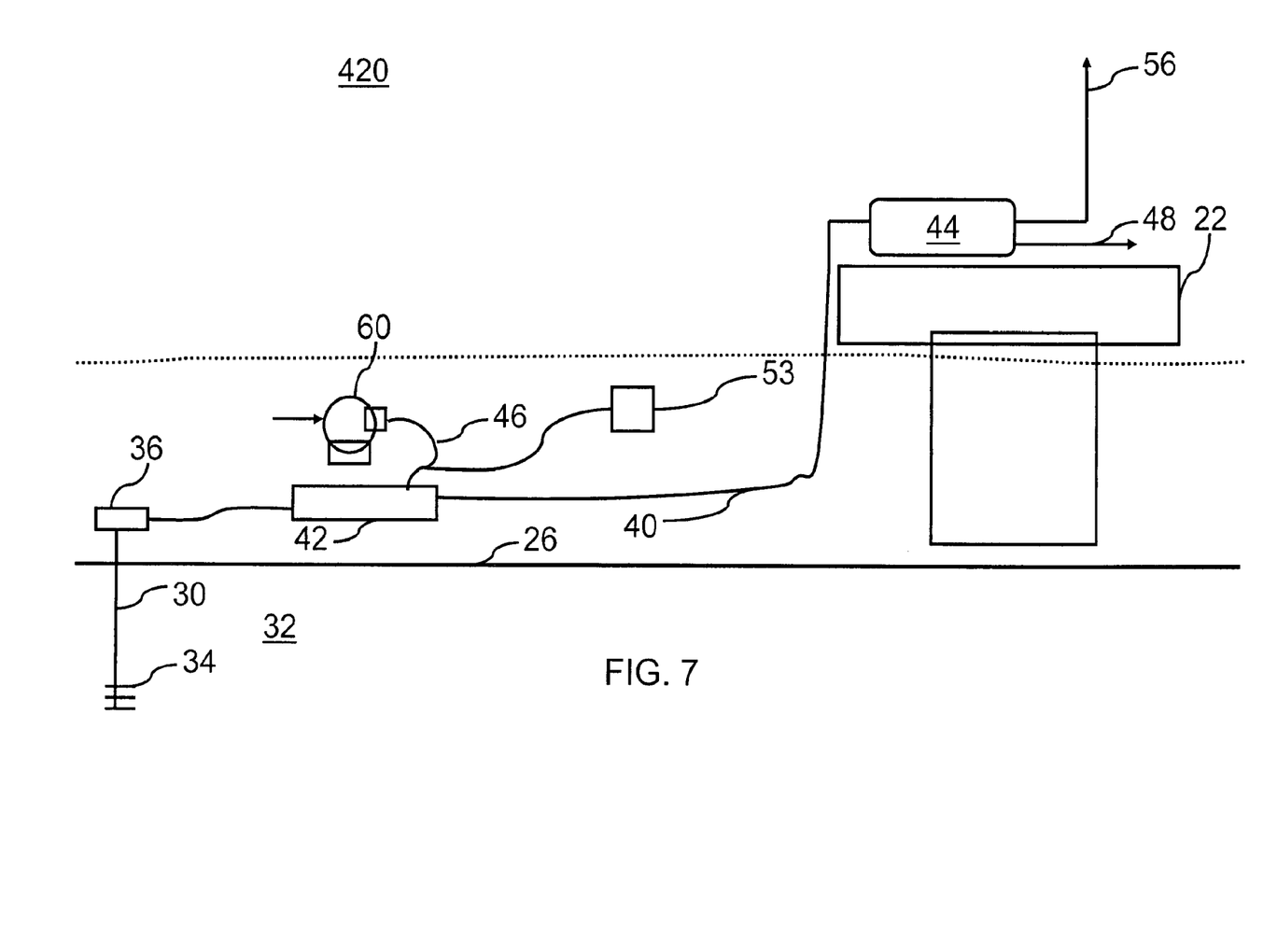
FIG. 7 is a fifth embodiment of a hydrate blockage inhibiting system using a submersible pump to inject sea water into a sub sea manifold.

FIGS. 6 and 7 show respective systems 320 and 420 wherein a submersible pump 60 gathers sea water and adds the extra water to production fluids to inhibit hydrate formation blockage. In system 320, the extra water is added to tree 36. In system 420, the extra water is added into the sub sea manifold 42. The advantage of using these systems 320 and 420 is that no lengthy water injection flow line 46 need be run from platform 22 to sea floor 26. A disadvantage is that additional amounts of water separated by separator 44 must be disposed because no water is reinjected into flow line 40.

Figure 8:
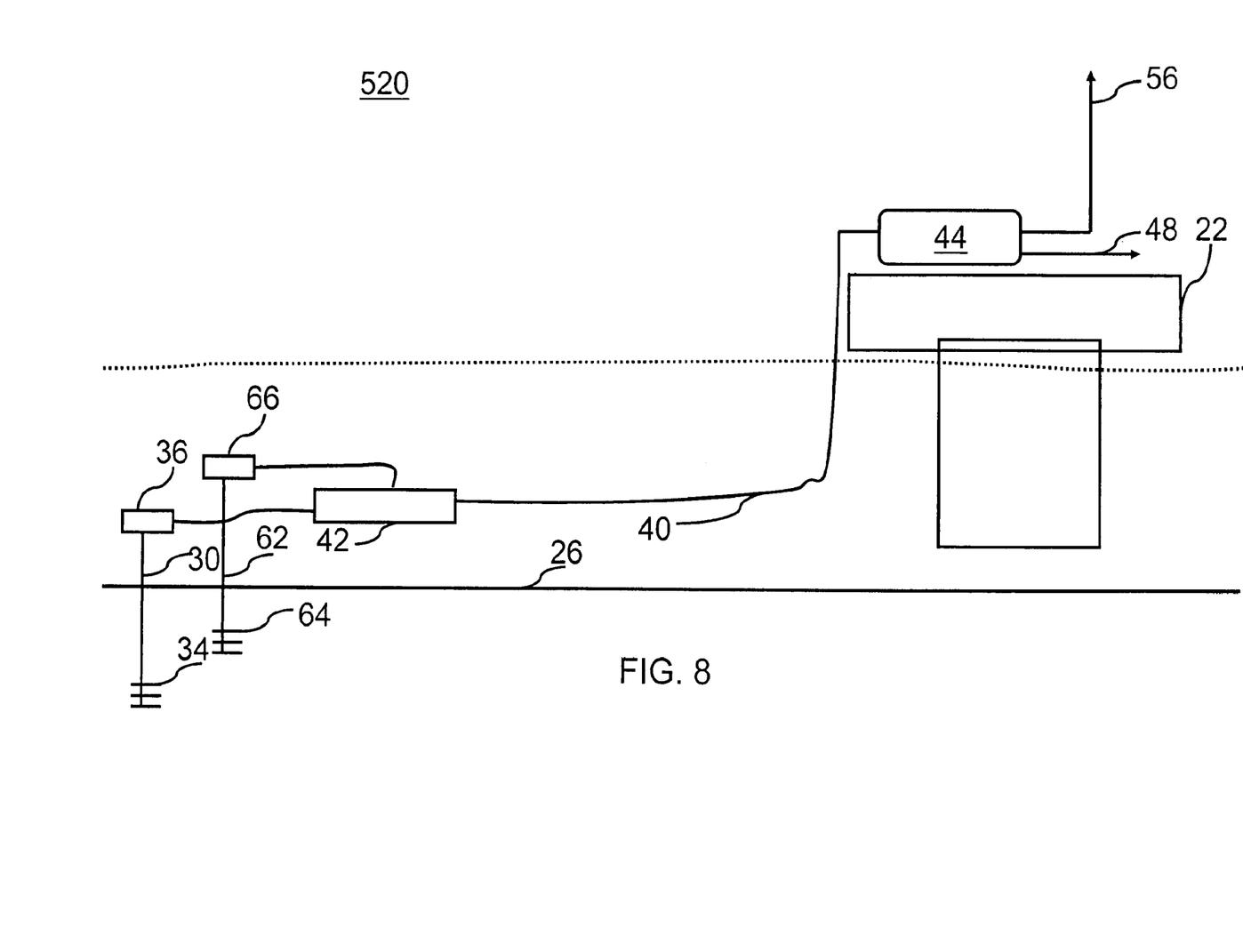
FIG. 8 is a sixth embodiment of a hydrate blockage inhibiting system which injects water from a sub sea well into a production fluid collected from a fresh water sub sea well.

FIG. 8 shows a system 520 wherein fresh water is injected into the production flow line 40. Production fluids from well bore 30 are collected by sub sea manifold 42. In this exemplary embodiment, a water well 62 is drilled into the sub sea formation 64 to provide a source of water. A well head 66 controls flow from well 62. Preferably, the source of water is fresh water having little brine. The water then can be added to the production fluid anywhere from downstream of the production zone, i.e. where perforations 34 are located to just upstream of where there is a significant potential for hydrate formation blockage to occur. In this particular exemplary embodiment, the added water is plumbed into sub sea manifold 42. Although not shown, a subset salt dispenser could also be used in embodiments 320, 420 and 520 if so desired to enhance the salinity of the water cut enhanced hydrocarbon containing fluids.

In a manner similar to that described above, the present invention could be used to add water to hydrocarbon containing fluids flowing in pipelines on land or elsewhere where hydrate formation blockage is a concern. For example, the pipeline may be operating in a cold and harsh environment such as in Alaska or Canada where plugging of pipelines and other conduits with hydrate formations is problematic.

In summary, this invention calls for multiphase production of crude oil and natural gas at high water cuts, possibly adding water/brine to forcibly push a flow system to higher water cuts. It is expected this strategy will allow operators to address multiple flow assurance issues (hydrate inhibition, emulsion viscosity/stability, system thermal performance, and system hydraulic performance) through a simple, cost-effective, environmentally friendly strategy.

While in the foregoing specification this invention has been described in relation to certain preferred embodiments thereof, and many details have been set forth for purpose of illustration, it will be apparent to those skilled in the art that the invention is susceptible to alteration and that certain other details described herein can vary considerably without departing from the basic principles of the invention.

That which is claimed is:

1. A method for inhibiting hydrate formation blockage in a flow line transporting a hydrocarbon containing fluid, the method comprising:
   adding water to a hydrocarbon containing fluid to produce a water cut enhanced hydrocarbon containing fluid, whereby the water cut enhanced hydrocarbon containing fluid consists of hydrocarbon containing fluid, water, and optionally salt or brine; and
   transporting the water cut enhanced hydrocarbon containing fluid through a flow line under conditions that would be conducive for the formation of hydrates in the original hydrocarbon containing fluid;
   whereby hydrate formation blockage is inhibited from forming within the flow line by the addition of the water.

2. The method of claim 1 wherein:
   sufficient water is added such that the water cut of the water cut enhanced hydrocarbon containing fluid is at least 50%.

3. The method of claim 1 wherein:
   sufficient water is added such that the water cut of the water cut enhanced hydrocarbon containing fluid is at least 75%.

4. The method of claim 1 wherein:
   sufficient water is added such that the water cut of the water cut enhanced hydrocarbon containing fluid is at least 85%.

5. The method of claim 1 wherein:
   sufficient water is added to lower the hydrate equilibrium temperature of the water cut enhanced hydrocarbon containing fluid by at least 2° F. relative to the original hydrocarbon containing fluid.

6. The method of claim 1 wherein:
   sufficient water is added to lower the hydrate equilibrium temperature of the water cut enhanced hydrocarbon containing fluid by at least 5° F. relative to the original hydrocarbon containing fluid.

7. The method of claim 1 wherein:
   salt is added to the water to increase the salinity of the water cut enhanced hydrocarbon containing fluid.

8. The method of claim 7 wherein:
   the weight % of salt in the water cut enhanced hydrocarbon containing fluid is at least 5%.

9. The method of claim 7 wherein:
   the weight % of the salt in the water cut enhanced hydrocarbon containing fluid is at least 10%.

10. The method of claim 7 wherein:
    the water phase of the water cut enhanced hydrocarbon containing fluid is continuous; and
    the water cut enhanced hydrocarbon containing fluid has a weight % of salt of at least 5%.

11. The method of claim 1 wherein:
    the water is added to the hydrocarbon containing fluid at a sub sea location.

12. The method of claim 1 wherein:
    sufficient water is added such that hydrate formation is self limiting as hydrocarbon hydrate forming components in the water cut enhanced hydrocarbon containing fluid are exhausted through the formation of hydrate particles.

13. The method of claim 1 wherein:
    sufficient water is added such that the hydrocarbon containing fluid is converted from a water-in-oil emulsion to a water-continuous emulsion thereby decreasing emulsion viscosity and reducing pressure drop in the flow line.

14. A system for preventing the formation of hydrate blockage in a flow line, the system comprising:
    a flow line for transporting a hydrocarbon containing fluid;
    a water injection conduit fluidly connected to the flow line to add water to the flow line, the water injection conduit being in fluid communication with one of a source of sea water, a source of fresh water, a subsea well or water produced from fluids from a hydrocarbon producing well bore; and
    a hydrocarbon source which is in fluid communication with the flow line to provide a hydrocarbon containing fluid to the flow line;
    wherein water may be added to the flow line from the water injection conduit to produce a water cut enhanced hydrocarbon containing fluid, whereby the water cut enhanced hydrocarbon containing fluid consists of hydrocarbon containing fluid, water, and optionally salt or brine.

15. The system of claim 14 wherein:
    the hydrocarbon source is a well bore.

16. The system of claim 14 further comprising:
    a water source fluidly connected to the water injection conduit; and the water source is one of sea water, a sub sea water well or a water source mounted on an offshore platform.

17. The system of claim 14 further comprising:
    a water separator fluidly connected to the flow line to receive fluids containing hydrocarbons and water, the water separator being capable of separating water from hydrocarbons.

18. The system of claim 17 wherein:
    the flow line, water separator and water injection conduit cooperate to form a loop wherein water from the flow line may be separated by the water separator and delivered back to the water injection conduit to be reinjected into the flow line.

19. The system of claim 14 further comprising:
    a salt dispenser which connects relative to the flow line so that salt may be added to increase the salinity of the hydrocarbon containing fluid.

20. The system of claim 14 wherein:
the water injection conduit is in fluid communication with a source of sea water.

21. The system of claim 14 wherein:
the water injection conduit is in fluid communication with a subsea well.

22. The system of claim 14 wherein:
the water injection conduit is in fluid communication with separated water produced from a hydrocarbon producing well bore.

23. The system of claim 14 wherein:
the water injection conduit is in fluid communication with a source of fresh water.

24. A method for inhibiting hydrate formation blockage in a flow line transporting a hydrocarbon containing fluid, the method comprising:
adding water to a hydrocarbon containing fluid to produce a water cut enhanced hydrocarbon containing fluid, wherein sufficient water is added such that the water cut of the water cut enhanced hydrocarbon containing fluid is at least 50% and whereby the water cut enhanced hydrocarbon containing fluid consists of hydrocarbon containing fluid, water, and optionally salt or brine; and
transporting the water cut enhanced hydrocarbon containing fluid through a flow line under conditions that would be conducive for the formation of hydrates in the original hydrocarbon containing fluid;
whereby hydrate formation blockage is inhibited from forming within the flow line by the addition of the water to form a slurry of hydrates and water.

25. A method for inhibiting hydrate formation blockage in a flow line transporting a hydrocarbon containing fluid, the method comprising:
adding water to a hydrocarbon containing fluid to produce a water cut enhanced hydrocarbon containing fluid, wherein sufficient water is added such that hydrate formation is self limiting as hydrocarbon hydrate forming components in the water cut enhanced hydrocarbon containing fluid are exhausted through the formation of hydrate particles and whereby the water cut enhanced hydrocarbon containing fluid consists of hydrocarbon containing fluid, water, and optionally salt or brine; and
transporting the water cut enhanced hydrocarbon containing fluid through a flow line under conditions that would be conducive for the formation of hydrates in the original hydrocarbon containing fluid;
whereby hydrate formation blockage is inhibited from forming within the flow line by the addition of the water to form a slurry of hydrates and water.

26. A method for inhibiting hydrate formation blockage in a flow line transporting a hydrocarbon containing fluid, the method comprising:
adding water to a hydrocarbon containing fluid to produce a water cut enhanced hydrocarbon containing fluid, wherein sufficient water is added such that the hydrocarbon containing fluid is converted from a water-in-oil emulsion to a water continuous emulsion thereby decreasing emulsion viscosity and reducing pressure drop in the flow line and whereby the water cut enhanced hydrocarbon containing fluid consists of hydrocarbon containing fluid, water, and optionally salt or brine; and
transporting the water cut enhanced hydrocarbon containing fluid through a flow line under conditions that would be conducive for the formation of hydrates in the original hydrocarbon containing fluid;
whereby hydrate formation blockage is inhibited from forming within the flow line by the addition of the water to form a slurry of hydrates and water.

* * * * *